United States Patent [19]

Dennehey et al.

[11] 4,201,406
[45] May 6, 1980

[54] SPIKE CONNECTOR FOR SOLUTION BAG

[75] Inventors: T. Michael Dennehey, Arlington Heights; Ludwig Wolf, Jr., Crystal Lake, both of Ill.

[73] Assignee: Baxter Travenol Laboratories, Inc., Deerfield, Ill.

[21] Appl. No.: 960,157

[22] Filed: Nov. 13, 1978

[51] Int. Cl.² .......... A61M 5/00; F16L 47/00
[52] U.S. Cl. .......... 285/3; 128/214.2; 128/272.3; 285/27
[58] Field of Search .......... 285/3, 4, 27; 128/214.2, 214 D, 272.3

[56] References Cited

U.S. PATENT DOCUMENTS

| | | | |
|---|---|---|---|
| 2,958,545 | 11/1960 | Stelzer | 285/3 |
| 3,193,310 | 7/1965 | Hildner | 285/27 |
| 3,201,148 | 8/1965 | Shurtleff | 285/3 |
| 3,976,073 | 8/1976 | Quick et al | 128/272 |
| 3,986,508 | 10/1976 | Barrington | 285/3 X |
| 4,019,512 | 4/1977 | Tenczar | 285/3 X |
| 4,022,205 | 5/1977 | Tenczar | 285/3 X |
| 4,022,496 | 5/1977 | Crissy et al. | 285/3 |

FOREIGN PATENT DOCUMENTS

| | | | |
|---|---|---|---|
| 1300635 | 8/1969 | Fed. Rep. of Germany | 285/3 |
| 1428391 | 1976 | United Kingdom. | |

*Primary Examiner*—Thomas F. Callaghan
*Attorney, Agent, or Firm*—Paul C. Flattery; George H. Gerstman

[57] ABSTRACT

A touch-contamination protected spike connector is provided for coupling a plastic fluid conduit to a port extending from a medical solution container. The spike defines a longitudinal bore and has an angled tip, and carries a flange which extends outwardly from the spike. A tube surrounds and is concentric with a major portion of the spike, with the tube having a dimension suited for coupling to the port with a snug pressure fit. A spacer is interposed between the spike and the tube. The flange and surrounding tube cooperate to enable the spike to be connected to the port with the chance of bacterial contamination caused by accidental touching of the spike being minimized.

5 Claims, 3 Drawing Figures

U.S. Patent    May 6, 1980    4,201,406
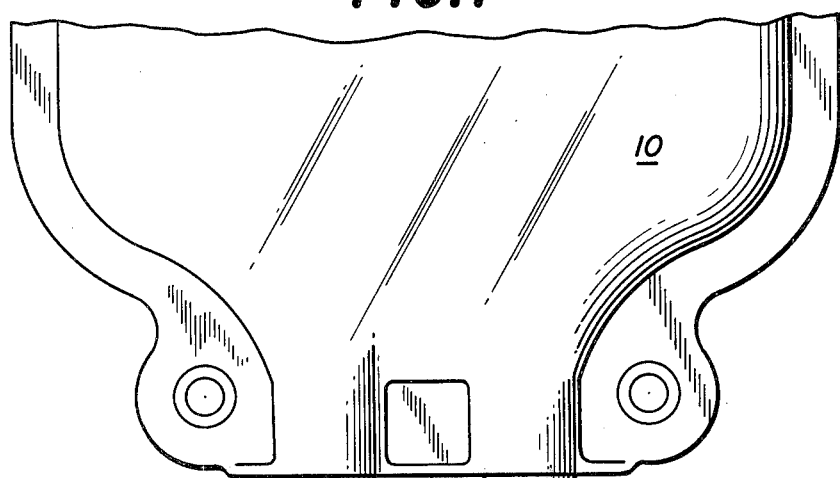
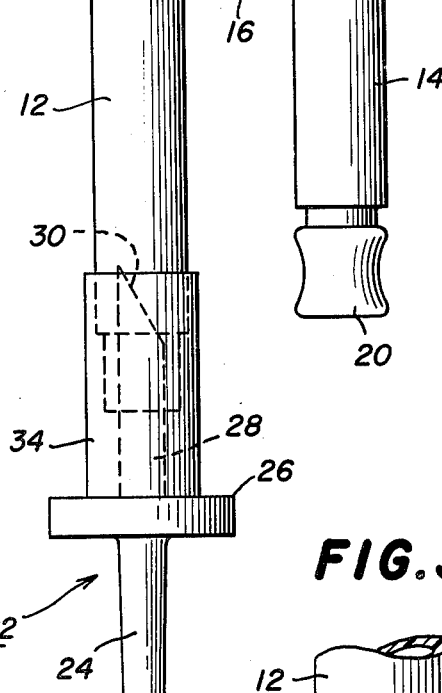
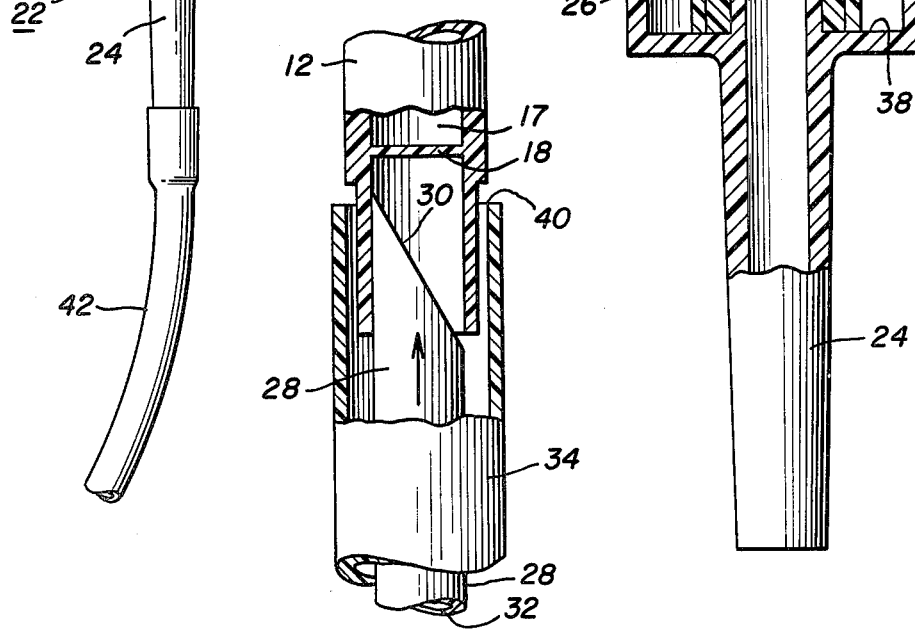

SPIKE CONNECTOR FOR SOLUTION BAG

BACKGROUND OF THE INVENTION

The present invention concerns a spike connector of the type that is used to connect a tubing set to a medical solution container.

Many medical solution containers typically have an outlet port extending therefrom, with the port having a transverse diaphragm adapted for breakage by a spike from a tubing set. When the spike is inserted into the port, the transverse diaphragm is broken and the medical liquid can flow from the medical container through the spike and the tubing set and to the patient.

In certain applications a sterile medical solution is utilized and it is important that the sterility of the system be maintained. For example, in peritoneal dialysis a dialysate solution is introduced into a patient's peritoneal cavity and is thereafter drained from the peritoneal cavity to the original solution container or elsewhere. One type of ambulatory peritoneal dialysis has been suggested in which a plastic container of dialysate solution is connected to tubing which is coupled to a catheter leading to the patient's peritoneal cavity. The dialysate solution within the flexible solution bag is introduced via the tubing to the patient's peritoneal cavity, the tubing is clamped and the solution bag is folded and carried by the patient for several hours while the dialysate solution remains in the patient's peritoneal cavity. After several hours, for example three or four hours, the solution bag is unfolded, the tubing is unclamped and the solution within the peritoneal cavity is drained into the same solution bag. Thereafter, the tubing is removed from the solution bag and is connected to a fresh solution bag and the aforesaid procedure is thereupon repeated.

One type of tubing connection to the solution bag discussed above is by utilizing a spike which is inserted into a port from the solution bag. As stated above, after the patient has drained the fluid from his peritoneal cavity back to the solution bag, he will thereupon connect the tubing to a fresh solution bag by removing the spike from the port of a used solution bag and inserting it into the port of a fresh solution bag. It can be seen that accidental touching of the spike would break sterility of the system and peritonitis may result.

It is, therefore, an object of the present invention to provide a spike connector that is touch-contamination protected.

Another object of the present invention is to provide a spike connector that can be used for connecting a tubing set to a port extending from a medical solution container, with the port having a transverse diaphragm adapted for breakage by the spike, and with the spike carrying means for minimizing bacterial contamination caused by accidental touching of the spike.

A further object of the present invention is to provide a touch-contamination protected spike connector which is simple in construction and is easy to manufacture.

Other objects of the present invention will become apparent as the description proceeds.

SUMMARY OF THE INVENTION

In accordance with the present invention, a touch-contamination protected spike connector is provided for coupling a plastic fluid conduit to a port extending from a medical solution container. The port has a transverse diaphragm adapted for breakage by the spike to provide communication from the plastic fluid conduit to the medical solution container.

The improvement comprises a rigid spike defining a longitudinal bore and having an angled tip. A flange extends outwardly from the rigid spike and a tube surrounds a major portion of the spike and extends in a generally parallel direction to the spike. The internal wall of the tube is spaced from the external wall of the spike. A spacer is interposed between the spike and the tube.

In the illustrative embodiment, the flange extends radially from the spike a greater radial distance than the tube's radial distance from the spike. The angled tip has a distal end which extends a greater distance than the tube in the longitudinal direction.

In the illustrative embodiment, a tip protector is included to cover the spike and is adapted for easy manual removal. The tube has a dimension suited for coupling to the port with a snug pressure fit.

A more detailed explanation of the invention is provided in the following description and claims, and is illustrated in the accompanying drawings.

BRIEF DESCRIPTION OF THE DRAWINGS

FIG. 1 is a view of a spike connector constructed in accordance with the principles of the present invention and coupled with the port of a medical solution container;

FIG. 2 is an enlarged cross-sectional elevation of the spike connector of FIG. 1; and FIG. 3 is a fragmentary view, partially in cross-section, of the spike connector being coupled to the port.

DETAILED DESCRIPTION OF THE ILLUSTRATIVE EMBODIMENT

Referring to FIG. 1, a conventional medical solution bag 10 is shown therein having ports 12 and 14 extending from one side 16 of the container 10. As shown in FIGS. 2 and 3, port 12 has an axial bore 17 and a transverse diaphragm 18 which blocks fluid flow from the container until the diaphragm 18 is broken. Port 14 is capped with an injection site 20 in the illustrative embodiment.

Although solution container 10 is illustrated as a flexible bag type of solution container, it is understood that the instant invention is applicable to rigid containers, such as glass bottles, and also to various types of medical procedures including but not limited to ambulatory peritoneal dialysis.

The spike connector generally designated by reference numeral 22 has a main portion preferably formed in a one-piece molded construction comprising a rear tubular connector portion 24, a radially extending flange 26 and a spike 28. The distal end of spike 28 comprises an angled tip 30 as is well-known in the art, and the spike 28 and connector portion 24 define an axial bore 32.

In the illustrative embodiment, spike 28 has a circular cross-sectional configuration. A tube 34 surrounds a major portion of spike 28 and is concentric therewith, with the tube extending in a generally parallel direction to the spike. A spacer such as a bushing 36 is interposed between spike 28 and tube 34 and extends from inside rear surface 38 of flange 26 in a direction toward tip 30. The spacer could be an integral portion of flange 26 if desired.

In the illustrative embodiment, flange 26 extends radially from spike 28 a greater radial distance than the radial distance of tube 34 from spike 28. As illustrated in FIGS. 1 and 2, the distal end of tip 30 extends a greater distance than the distal end 40 of tube 34.

It is preferred that bushing 36 be formed of a resilient plastic material and it is seen that the bushing fills a portion of the volume between spike 28 and tube 34. In producing the touch protected spike connector, the one-piece molded item including the connector portion 24, flange 26 and spike 28 is modified by gluing or otherwise adhering bushing 36 over the spike, as illustrated in FIG. 2, and then pressing, gluing or otherwise adhering tube 34 to bushing 36. Spike 28 is preferably formed of a material having a relatively slippery surface so that the spike can be inserted easily into port 12. Lubricating material may be applied to the spike and may comprise silicone or other lubricating materials as are well-known in the art.

Tubing 34 is preferably formed of either Teflon ® polytetrafluoroethylene or a polyolefin material or an ethylene vinyl acetate copolymer. The extension of the distal end of tip 30 past the distal end 40 of tube 34 is helpful in aiding the alignment of the spike connector with port 12. In the illustrative embodiment, tube 34 has an internal diameter that is suited for enabling the tube to be coupled to port 12 with a snug pressure fit.

A tip protector may be utilized which covers the spike and maintains the sterile condition of the spike. The tip protector would be of a type which is adapted for easy manual removal.

It can be seen that the touch protected spike connector is simple in construction and includes a connector portion to which tubing 42 from a tubing set is connected. The operator can connect the spike into the port 12 without accidentally touching the spike and the engagement of the tube 34 over the end of port 12 aids in preventing bacterial contamination.

Bushing 36, which is preferably formed of a resilient vinyl material, serves to operate as an aligning device or a spacer for tube 34, thereby maintaining the concentricity of the tube 34 with respect to spike 28.

Although an illustrative embodiment of the invention has been shown and described, it is to be understood that various modifications and substitutions may be made by those skilled in the art without departing from the novel spirit and scope of the present invention.

What is claimed is:

1. A touch-contamination protected spike connector for coupling a plastic fluid conduit to a port extending from a medical solution container, the port having a transverse diaphragm adapted for breakage by the spike to provide communication from the plastic fluid conduit to the medical solution container, the improvement comprising:

a rigid spike defining a longitudinal bore and having an angled tip;

a flange extending radially outwardly from said rigid spike;

a tube surrounding a major portion of said spike and extending in a generally parallel direction to said spike with the internal wall of said tube being spaced from the external wall of said spike;

a spacer immovably interposed between the spike and the tube, said spacer being formed of resilient material and being connected to said flange and filling a portion of the volume between said spike and said tube;

said angled tip having a distal end which extends a greater distance than said tube in the longitudinal direction.

2. A spike connector as described in claim 1, said flange extending radially from said spike a greater radial distance than the tube's radial distance from the spike.

3. A spike connector as described in claim 1, said spike having a generally circular cross-sectional configuration and said tube being generally concentric therewith.

4. A spike connector as described in claim 1, said spacer being formed of a vinyl material and said tube being formed of an ethylene vinyl acetate copolymer.

5. A spike connector as described in claim 1, said tubing being formed of a material from the group consisting of Teflon ® polytetrafluoroethylene, a polyolefin, and an ethylene vinyl acetate copolymer.

* * * * *